(12) United States Patent
Huyghe et al.

(10) Patent No.: US 8,142,506 B2
(45) Date of Patent: Mar. 27, 2012

(54) PROSTHESIS MADE OF A FIBRE-REINFORCED HYDROGEL, METHOD OF MANUFACTURING THE PROSTHESIS AND USE THEREOF

(75) Inventors: Jacques Marie René Jan Huyghe, Eindhoven (NL); Corrinus Cornelis Van Donkelaar, Eindhoven (NL); Marcellus Wilhelmus Wijlaars, Venlo (NL); Gijsbertus Jacob Verkerke, Groningen (NL); Marcus Franciscus Eijkelkamp, Groningen (NL); Albert Gerrit Veldhuizen, Groningen (NL)

(73) Assignee: Technische Universiteit Eindhoven (NL)

( * ) Notice: Subject to any disclaimer, the term of this patent is extended or adjusted under 35 U.S.C. 154(b) by 0 days.

(21) Appl. No.: 10/564,518

(22) PCT Filed: Jul. 8, 2004

(86) PCT No.: PCT/NL2004/000495
§ 371 (c)(1),
(2), (4) Date: Mar. 1, 2007

(87) PCT Pub. No.: WO2005/013863
PCT Pub. Date: Feb. 17, 2005

(65) Prior Publication Data
US 2007/0179606 A1  Aug. 2, 2007

(30) Foreign Application Priority Data
Jul. 15, 2003 (NL) .................................... 1023926

(51) Int. Cl.
*A61F 2/44* (2006.01)

(52) U.S. Cl. ............ 623/17.15; 623/17.11; 623/17.12; 623/17.13; 623/17.16

(58) Field of Classification Search .............. 606/61, 606/246; 623/17.11–17.16
See application file for complete search history.

(56) References Cited

U.S. PATENT DOCUMENTS

| | | | | |
|---|---|---|---|---|
| 3,867,728 A * | 2/1975 | Stubstad et al. | ........... | 623/17.16 |
| 5,047,055 A * | 9/1991 | Bao et al. | ........... | 623/17.16 |
| 5,458,643 A * | 10/1995 | Oka et al. | ........... | 623/17.16 |
| 6,264,695 B1 * | 7/2001 | Stoy | ........... | 623/17.16 |
| 6,533,817 B1 | 3/2003 | Norton et al. | | |
| 6,726,721 B2 * | 4/2004 | Stoy et al. | ........... | 623/17.16 |
| 7,008,635 B1 * | 3/2006 | Coury et al. | ........... | 424/426 |
| 7,066,960 B1 * | 6/2006 | Dickman | ........... | 623/17.16 |
| 2003/0045939 A1 | 3/2003 | Casutt | | |

FOREIGN PATENT DOCUMENTS

| | | |
|---|---|---|
| EP | 0 346 129 A1 | 12/1989 |
| WO | WO 02/17824 A2 | 3/2002 |
| WO | WO 02/17824 A3 | 3/2002 |
| WO | WO 2004/049980 A1 | 6/2004 |

\* cited by examiner

*Primary Examiner* — Thomas Barrett
*Assistant Examiner* — Andrew Yang
(74) *Attorney, Agent, or Firm* — Shumaker, Loop & Kendrick, LLP

(57) ABSTRACT

The present application relates to a prosthesis comprising a flexible portion (1) and at least one less flexible portion (2), which flexible portion comprises a fiber-reinforced hydrogel. In addition to that, the application relates to a prosthesis consisting of a fiber-reinforced hydrogel, which prosthesis is intended to replace cartilaginous materials. The application further relates to the use of the prosthesis and to a method for manufacturing the prosthesis. The application furthermore relates to a method of preparing the flexible portion for a prosthesis. Finally, the application relates to a fiber material apparently intended for use in the prosthesis.

24 Claims, 1 Drawing Sheet

US 8,142,506 B2

PROSTHESIS MADE OF A FIBRE-REINFORCED HYDROGEL, METHOD OF MANUFACTURING THE PROSTHESIS AND USE THEREOF

BACKGROUND

The present invention relates to a prosthesis comprising a flexible portion and at least one less flexible portion. In addition to that, the invention relates to a prosthesis consisting of a fibre-reinforced hydrogel. The invention further relates to the use of the prosthesis and to a method of manufacturing the prosthesis. The invention furthermore relates to a method of preparing the flexible portion for a prosthesis. Finally, the invention relates to a fibre material apparently intended for use in the prosthesis.

Prostheses for intervertebral discs must meet a number of requirements (Eijkelkamp et al., *The International Journal of Artificial Organs,* 2001, 21(5), 311-321), inter alia a correct geometry for an optimum adhesion and an optimum distribution of the pressure in relation to the adjacent vertebrae, in addition to that stiffness, in order to obtain a proper shock-absorbing action, and a swelling behaviour comparable to that of the natural intervertebral disc.

US Patent Application 2003/0045939 relates to an artificial intervertebral disc, comprising two end plates, which bound a hollow space, which is filled with an elastically and/or plastically deformable nucleus, with the hollow space being enclosed by a tubular fibre ring, made up out of for example polyamide, polyimide or polyethylene terephthalate.

U.S. Pat. No. 6,533,817 discloses a prosthetic disc nucleus apparatus, comprising a prosthetic disc nucleus for implantation, including a hydrogel core, configured to hydrate from a dehydrate state following implantation, and a retainer.

International application WO 02/17824 relates to an intervertebral disc nucleus implant, comprising a load bearing elastic body, surrounded by a resorbable shell, comprised of for example fibrin, gelatin and polymers, such as polyethylene oxide, polyethylene glycol and polyvinyl alcohol.

European patent application 0 346 129 relates to an intervertebral disc spacer, comprising a central core of biocompatible elastomer and laminae wrapping said central core comprised of strips of sheets of a reinforcing fiber embedded in a biocompatible elastomer and endplates.

U.S. Pat. No. 5,047,055 discloses a prosthetic nudes for a vertebral disc made of a biocompatible hydrogel material.

The natural intervertebral disc (discus intervertebralis) is a cartilaginous disc which connects the vertebrae. A disc is built up of a gelatinous core (nucleus pulposus) enveloped in a fibrous ring (annulus fibrosus) (White et al., *Clinical biomechanics of the spine*, J.B. Lippencott Company, Philadelphia, 1978)). The nucleus and the annulus contain rigid collagen fibres, which are intertwined with proteoglycan chains. Said proteoglycans contain fixed, strongly negatively charged side chains (glycosaminoglycans), which interact with ions from the environment, as a result of which water is attracted by the disc. On account of the high concentration of proteoglycans, the nucleus contains 85-95% water, whereas the annulus, which comprises a relatively great deal of collagen fibres and less proteoglycans, contains 70-85% water. As a result of this specific composition, the disc allows movement of the vertebrae relative to each other and, in addition, has a shock-absorbing function. The two adjacent vertebrae comprise end plates consisting of hyalin ("vitreous") cartilage, which serves as a transition zone between the soft intervertebral disc and the hard vertebrae.

In the case of back trouble associated with degeneration of the disc, such as a serious hernia nucleus pulposus, surgery may be necessary. In some cases part of the disc may be saved, but in serious cases the disc must be replaced in its entirety. To restore the function of the vertebral column, a prosthesis must be implanted which takes over the mechanical function of the disc both as regards its mechanical stiffness and as regards its swelling behaviour.

Examples of commercially available prostheses for replacing intervertebral discs include: a rubber core covered by titanium end plates (Acroflex®) and a polyethylene core covered by cobalt/chromium end plates (Charité®); Prostheses intended for replacing the nucleus of an intervertebral disc, which are made of hydrogel materials are known, inter alia from U.S. Pat. Nos. 5,674,295; 6,402,784 and 5,047,055, in which the annulus is filled with a hydrogel having swelling characteristics, which may or may not be surrounded by a membrane.

A fibre-reinforced hydrogel material is known from "Composite hydrogels for implants": L. Ambrosio & Co., *Proceedings of the institution of mechanical engineers*, part H, *Journal of Engineering in Medicine* (1998), 212 (2), 93-9, Ref. 24. Use is made therein of bundles of non-absorbent polyethylene terephthalate fibres, which are incorporated in the polymerised hydrogel. For a number of uses, the material that is obtained therewith is stiff in comparison with the characteristic stiffness of the soft biological tissues that it aims to replace.

Young et al. (*Biomaterials* 1998, 19, 175-1752) describes a material with a base of Lycra (brand) fibre-reinforced poly-2-hydroxy ethyl methacrylate (pHEMA). Knitted or woven fibre structures are provided in a hydrogel. The fibre-reinforced hydrogel contains about 1% fibre and may be used as artificial skin.

SUMMARY OF THE INVENTION

The object of the present invention is to provide a prosthesis made of a material which combines a low degree of stiffness with a high degree of toughness.

This object is accomplished by the present invention. The invention relates to a prosthesis consisting of a flexible portion and at least one less flexible portion, which flexible portion comprises a fibre-reinforced hydrogel.

This has the advantage that the less flexible portion may be used for retaining the correct shape of the prosthesis, for example, or as a location for adhering the prosthesis to the surrounding tissue.

The invention also relates to a prosthesis consisting of a fibre-reinforced hydrogel, which prosthesis functions to replace cartilaginous materials. A preferred cartilaginous material in which the present prosthesis may be used is an intervertebral disc.

The prosthesis according to the present invention may be used in particular for replacing cartilaginous materials, because the structure and the characteristics of the prosthesis are quite similar to those of cartilaginous materials.

The invention furthermore relates to a prosthesis consisting of a fibre-reinforced hydrogel, which prosthesis functions to replace cartilaginous materials, wherein the prosthesis comprises at least one less flexible portion.

As described above, a less flexible portion has this advantage that it may be used for retaining the correct shape of the prosthesis or as a location for adhering the prosthesis to the surrounding tissue.

In addition, the invention relates to a prosthesis in which the less flexible portion is present on a bottom side and/or on an upper side of the flexible portion.

Said less flexible portions provide a location where the prosthesis can adhere to the surrounding tissue in which the prosthesis is to be implanted, so as to ensure an optimum adhesion and an optimum pressure distribution.

In one embodiment, the less flexible portion is an end plate, the advantage being that the geometry can easily be adapted to the environment in which the prosthesis is to be used.

The invention also relates to a prosthesis in which the less flexible portion is present on an inner side of the flexible portion.

This has the advantage that prosthesis geometries are possible which are completely different from the geometry that is obtained when the less flexible portions are present on the upper side and on the bottom side.

In a preferred embodiment, the prosthesis functions to replace an intervertebral disc in whole or in part.

The advantage of the prosthesis is that it may be used for replacing only the nucleus as well as for replacing the whole of nucleus and annulus of an intervertebral disc.

The flexible portion of the prosthesis according to the present invention furthermore has swelling characteristics comparable to those of a natural intervertebral disc. This has the advantage that the prosthesis—just like the natural intervertebral—is capable of exuding bodily fluid during the day under the influence of the pressure and the movements of the body and of absorbing bodily fluid during the night.

According to a preferred embodiment, the flexible portion of the prosthesis according to the invention consists of a slice of a fibre-reinforced hydrogel having a thickness of 5-15 mm, in particular having a thickness of 8-10 mm.

The inventors have found that this geometry is especially advantageous for specific uses.

In addition to that, the fibre-reinforced hydrogel according to the present invention comprises at least 5% fibres.

The inventors have found that this fibre concentration provides the best results as regards the desired characteristics of the final material.

The invention also relates to the use of the prosthesis, which is implanted into humans or animals.

According to one embodiment, the present invention relates to a method of using the prosthesis, wherein the volume of the prosthesis is reduced prior to implantation by extracting water therefrom.

This has the advantage that fewer complications occur during implantation of the prosthesis because the ligaments need not be stretched and/or cut through, since the prosthesis is smaller in size upon being implanted and will assume its desired shape after being implanted into the body.

According to another embodiment of the invention, the volume of the prosthesis is reduced by immersing it in a hypertonic salt bath.

The inventors have found that this is the most natural way of reducing the volume of the material. It has become apparent that the volume of the material increases as the salt concentration in the external salt bath decreases.

The invention furthermore relates to a method of manufacturing the prosthesis, wherein the fibres can be provided on the whole of the flexible portion and/or at least one less flexible portion by winding. The advantage of this method is that anisotropy is introduced into the design through fibre reinforcement comparable with the way in which fibres are arranged in the natural annulus. The fibre orientation can be optimised for the intended use by using suitable winding or knitting techniques.

According to a preferred embodiment of the invention method according to the invention, the angle at which the fibres are arranged with respect to an axis of rotation varies from 5° to 90°, in particular from 45° to 60°.

Research carried out by the present inventors has shown that the present method provides a material in which the fibre orientation is optimised.

One embodiment of the invention comprises a method of preparing the flexible portion for a prosthesis, wherein a bar of the hydrogel is formed, from which bar slices are cut. The advantage of this method is that several prostheses can be prepared from a hydrogel in a simple manner, providing the correct geometry for the prosthesis for specific uses.

In a preferred embodiment, said hydrogel is a fibre-reinforced hydrogel. This has the advantage that the hydrogel is stronger compared to the situation in which no fibres are used.

In a method according to the present invention, the slices are cut by setting up the bar in a lathe and moving a knife through the bar.

This has the advantage that the geometry and the thickness of the slice of hydrogel can be precisely determined. In a preferred method, the knife is lubricated during use. This has the advantage that a smoother surface of the slice of hydrogel is obtained.

The invention further relates to a fibre material apparently intended for use in the prosthesis, in which the fibres have a low elasticity modulus. This has the advantage that an optimised adhesion is provided between the hydrogel and the fibres in the prosthesis according to the present invention. By using a fibre having a low elasticity modulus, the forces acting on the interface between the fibre and the hydrogel are minimised.

The invention further relates to a fibre material in which the fibres are capable of absorbing monomers of the hydrogel. Due to this property, the composite material can be produced by previously immersing the fibres in the monomer bath, having the aforesaid absorption take place and subsequently initiating the polymerisation of the hydrogel matrix. Said polymerisation not only takes place in the hydrogel matrix of the composite, but also in the fibre. In this way a material is obtained in which the adhesion of the fibre to the hydrogel matrix is very good. It has become apparent that the materials used are not hydrophilic to pure water. In combination with one or more monomers, which provide the hydrogel matrix upon polymerisation, hydrophilic properties are obtained, however, and a very strong bond with the hydrogel matrix is obtained in combination with the special elastic behaviour of the fibres. The penetration of the monomer solution into the fibre causes the volume of the fibre to increase (>50%).

Finally, the invention relates to a fibre material in which the fibres are polyurethane-based.

It has been found that polyurethane fibres, in particular Lycra (brand) exhibit a stiffness in the same order as the hydrogel at a low tension, and in addition to that they have the advantageous property that they absorb part of the monomer mixture for the hydrogel.

The invention will be explained in more detail in the following description, in which reference is made to the appended, non-limitative drawings, in which:

DETAILED DESCRIPTION

Figure 1:
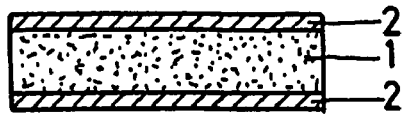
FIG. 1 shows the structure of the whole of a flexible portion (1) and less flexible portions (2) as part of the present invention.

FIG. 1 shows an embodiment of the present invention in which a base for a prosthesis for replacing an intervertebral disc is shown. Said base comprises a flexible portion (1) in the centre thereof, which is enclosed by less flexible portions (2) on the upper side and on the bottom side.

Figure 2:
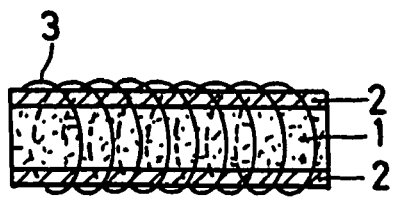
FIG. 2 shows the structure of the prosthesis according to the present invention, comprising a flexible portion (1) and less flexible portions (2) and fibres (3) provided all around for reinforcing purposes.

FIG. 2 shows an embodiment for a prosthesis according to the present invention in which, as shown in FIG. 1, the whole is reinforced with fibres (3), which are provided around the whole of (1) and (2).

A fibre of the type of Lycra (Dupont de Nemours) or Spandex (brand) is taken as an example. Lycra fibres consist of a polyurethane and can be stretched up to eight times their original length.

The monomers from which the hydrogel according to the present invention can be obtained by polymerisation may comprise HEMA and sodium methacrylate, among other substances. Other monomers, whether or not in combination with each other and with the aforesaid substances, are also possible. The hydrophilic nature of said monomers may be based on adsorption as well as on electrostatic attraction of hydrophilic cations by a permanent charge. The polymerisation process may be initiated by chemical, thermal or optical (UV radiation) means. It has become apparent that a material obtained in such a manner attains a compression strength in the order of several MPa, whilst the weight percentage of water is higher than 50%.

Figure 3:
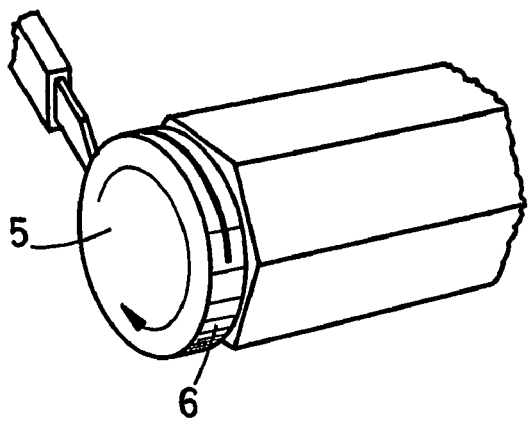
FIG. 3 shows a device for cutting a slice of hydrogel (5) from a bar of hydrogel (6).

An example of a method of manufacturing a flexible portion (1) of hydrogel according to the present invention comprises the cutting of slices (5) of 5-15 mm, preferably 8-10 mm, from a polymerised bar (6) of hydrogel, as shown in FIG. 3, which is made by polymerising a solution of at least one hydrogel monomer in a bar-shaped mould, using at least one polymerisation process.

Figure 4:
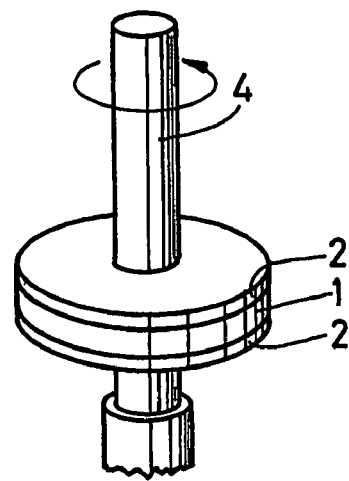
FIG. 4 shows a device for providing fibres (3) on the whole of a flexible portion (1) of hydrogel and less flexible portions on a rotating shaft.

One method according to the present invention for manufacturing the prosthesis concerns the provision of fibres around the whole of the flexible portion (1) and at least one less flexible portion (2). FIG. 4 shows a preferred method, in which the whole of the flexible portion (1) of hydrogel and the less flexible portions (2) is set up on a rotating shaft (4), after which the fibres (3) are provided around the whole of (1) and (2) by winding, as is shown in FIG. 5.

Figure 5:
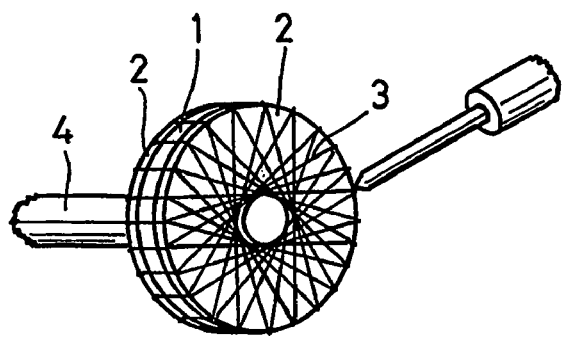
FIG. 5 shows a device for providing fibres (3) on the whole of a flexible portion (1) of hydrogel and less flexible portions by winding.

In one method according to the present invention, which is carried out by using a device as shown in FIG. 5, anisotropy is introduced into the design through fibre reinforcement comparable with the way in which fibres are arranged in the natural annulus. Part of the fibres, or all fibres, may be provided in the hydrogel as "chopped fibres". Using the construction according to the present invention, variations in the mechanical properties of the prosthesis can be effected in a simple manner. In the first place, variations in the composition of the hydrogel can influence the swelling behaviour. In the second place, it is possible to impart different mechanical properties for different directions of movements to the prosthesis by varying the fibre reinforcement on the geometry of the prosthesis.

According to a preferred method, the fibre is stretched to 1-6 times, preferably 3 times its original length during provision of the fibre, so as to ensure homogeneous properties for the entire fibre reinforcement. This makes it possible to provide several layers of fibre material, preferably dozens or even hundreds of layers, in which the angle of the fibres at the side with respect to the axis of rotation is varied from 5° to 90°, preferably from 45° to 60°, during provision of the fibres.

It is also possible to use other methods of providing fibres around the whole of the flexible portion and at least one less flexible portion, in particular other winding or knitting techniques. According to a preferred embodiment, the whole of the flexible portion and possibly a less flexible portion consisting of a fibre-reinforced hydrogel is immersed in a hydrogel monomer bath so as to produce the composite material as described above by having adsorption of the monomer to the fibres take place and subsequently initiating the polymerisation of the hydrogel so as to obtain the prosthesis according to the present invention.

According to a special embodiment of the invention, the less flexible portions (2) of the prosthesis consists of a hardened portion of polymerised hydrogel material at the upper side and the bottom side of the flexible portion (1). According to a preferred embodiment of the present invention, the less flexible portions (2) consist of separate end plates, which cover the upper side and the bottom side of the flexible portion (1) of hydrogel. Said less flexible portions (2) ensure that the fibres (3) are distributed homogeneously upon provision thereof, they prevent fibres from carving into the hydrogel and provide a location where the prosthesis can adhere to the adjacent vertebrae. The geometry of the less flexible portions (2) is preferably adapted to the geometry of the joint or the vertebra into which the prosthesis is to be implanted so as to ensure an optimum adhesion and pressure distribution. The geometry and the material of the prosthesis may be varied and selected by those skilled in this field of the art.

The swelling characteristics of the prosthesis according to the present invention may be used for simplifying surgery. A frequent complication during surgery is the necessity to stretch and/or cut the ligaments of the vertebrae through upon implantation of the prosthesis. Since the prosthesis is implanted in its final state, the adjacent vertebrae must be kept apart during surgery so as to make it possible to insert the prosthesis. In the long run, said overstretching of the ligaments may lead to calcification of the ligaments. The prosthesis according to the present invention may be placed in a salt bath prior to surgery so as to reduce its volume. This reduces the extent to which the ligaments of the vertebrae are overstretched during surgery and thus the risk of short-term as well as long-term complications, and in addition it accelerates the healing process after surgery.

Once the prosthesis according to the present invention is implanted in the body, osmotic action of the negatively charged groups in the hydrogel will cause it to absorb water in such a manner that it will assume the desired shape and the desired volume, filling the cavity between the adjacent vertebrae. Subsequently, the prosthesis—like the natural disc—will exude bodily fluid during the day and absorb it during the night.

The invention will now be explained in more detail by means of the following example.

Example

A monomer mixture of a hydrogel having a composition of HEMA is polymerised for 16 hours in a glass tube (22 mm diameter) in a water bath having a temperature of 45° C. Following that, the bar-shaped hydrogel material is removed from the glass tube and the two ends are cut off. The middle part is clamped in a metal tube, which is set up on the rotating part of a lathe as shown in FIG. 3. A knife is moved slowly (10 mm/min) through the hydrogel bar (6) whilst being lubricated with a Teflon spray, during which operation the bar (6) rotates at a speed of 100 revolutions per minute. Two end plates having a diameter of 22 mm and a thickness of 0.5 mm are provided at the upper side and the bottom side of the slice of hydrogel (5), and the whole is placed on a rotating shaft (4) as shown in FIG. 4.

Subsequently, Lycra fibres are provided by winding whilst being stretched to three times their original length. Three layers are provided, with the fibres being provided in such a manner that the angle they include with the rotating shaft is 45-60°. This angle is varied during the winding operation. The fibre is provided in 7500 revolutions. After winding, the whole of the flexible portion (1) of hydrogel enclosed between end plates (2) and wrapped in fibres (3) is immersed in a bath of hydrogel monomer (HEMA) so as to impregnate the fibres with the monomer. The prosthesis according to the present invention is obtained after polymerisation of the hydrogel under the influence of ultraviolet light.

Although the invention has been described above by means of special embodiments and an example, obvious variants will suggest themselves to those skilled in this field of the art after reading the foregoing, which variants fall within the scope of the appended claims.

The invention claimed is:

1. A prosthesis comprising a flexible portion and at least one less flexible portion, wherein said flexible portion comprises a fibre-reinforced hydrogel containing chopped fibres, the hydrogel comprising charged groups, characterized in that fibres are wound around and encompass the whole of the flexible portion and the at least one less flexible portion to reinforce the prosthesis.

2. The prosthesis according to claim 1, characterized in that said less flexible portion is provided on a bottom side and/or an upper side of said flexible portion.

3. The prosthesis according to claim 1, characterized in that said less flexible portion is an end plate.

4. The prosthesis according to claim 1, characterized in that said less flexible portion is provided on an inner side of said flexible portion.

5. The prosthesis according to claim 1, characterized in that said prosthesis is for replacement of a joint in a human or animal.

6. The prosthesis according to claim 5, characterized in that said prosthesis is for replacement of a part or the whole of an intervertebral disc.

7. The prosthesis according to claim 1, characterized in that said flexible portion has swelling characteristics comparable to those of a natural intervertebral disc.

8. The prosthesis according to claim 1, characterized in that said flexible portion consists of a slice of a fibre-reinforced hydrogel having a thickness of 5-15 mm.

9. The prosthesis according to claim 8, characterized in that said slice of fibre-reinforced hydrogel has a thickness of 8-10 mm.

10. The prosthesis according to claim 1, characterized in that said fibre-reinforced hydrogel comprises at least 5% fibres.

11. A prosthesis consisting of the prosthesis of claim 1, characterized in that the prosthesis is intended to replace cartilaginous materials.

12. A method of using a prosthesis comprising implanting the prosthesis of claim 1 in a human or an animal.

13. The method for according to claim 12, characterized in that the volume of the prosthesis is reduced prior to the implantation thereof by extracting water therefrom.

14. The method according to claim 13, characterized in that the volume of the prosthesis is reduced by immersing it in a hypertonic salt bath.

15. A method for manufacturing the prosthesis according to claim 1, characterized in that the fibres are provided around the whole of the flexible portion and at least one less flexible portion by winding to reinforce the prosthesis.

16. The method according to claim 15, characterized in that the angle at which the fibres are arranged with respect to an axis of rotation varies from 5° to 90°.

17. The method according to claim 16, characterized in that said angle varies from 45° to 60°.

18. The prosthesis according to claim 1, characterized in that the flexible portion is prepared by forming a bar of the hydrogel from which slices are cut.

19. The prosthesis according to claim 18, characterized in that said slices are cut by setting up the bar on a lathe and moving a knife through the bar.

20. The prosthesis according to claim 19, characterized in that said knife is lubricated during cutting.

21. The prosthesis according to claim 1, characterized in that said fibres wound around the flexible portion have a low elasticity modulus.

22. The prosthesis according to claim 21, characterized in that said fibres wound around the flexible portion are capable of absorbing hydrogel monomers.

23. The prosthesis according to claim 21, characterized in that said fibres wound around the flexible portion are made of polyurethane.

24. The prosthesis according to claim 1, wherein the hydrogel comprises negatively charged groups, such that the hydrogel is configured to absorb fluid by osmotic action when the hydrogel is at rest.

* * * * *